(12) United States Patent
Schacher et al.

(10) Patent No.: US 8,361,387 B2
(45) Date of Patent: Jan. 29, 2013

(54) SYSTEM AND METHOD FOR THE PROCESSING OF LIQUID SAMPLES

(75) Inventors: Gottlieb Schacher, Kriens (CH); Rolf Sigrist, Vitznau (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 525 days.

(21) Appl. No.: 12/623,748

(22) Filed: Nov. 23, 2009

(65) Prior Publication Data

US 2010/0132484 A1 Jun. 3, 2010

(30) Foreign Application Priority Data

Nov. 28, 2008 (EP) ..................................... 08170322

(51) Int. Cl.
*G01N 35/02* (2006.01)
*G01N 35/10* (2006.01)
(52) U.S. Cl. ..................... 422/63; 73/863.01; 73/863.11; 422/65; 422/509; 422/510; 436/174
(58) Field of Classification Search ....... 73/863–863.01, 73/863.11, 864.01, 864.91; 422/63, 65, 509–510, 422/512, 922; 436/43, 47–48, 50, 55, 174, 436/180
See application file for complete search history.

(56) References Cited

U.S. PATENT DOCUMENTS

| | | | |
|---|---|---|---|
| 5,147,610 A * | 9/1992 | Watanabe et al. | 422/63 X |
| 5,814,276 A * | 9/1998 | Riggs | 422/65 |
| 5,814,277 A | 9/1998 | Bell et al. | |
| 6,425,296 B1 * | 7/2002 | Brust et al. | 73/863.23 |
| 6,478,524 B1 | 11/2002 | Malin | |
| 6,537,434 B1 * | 3/2003 | McGrath et al. | 422/63 X |
| 6,752,960 B1 * | 6/2004 | Matsubara et al. | 422/63 |
| 6,891,182 B2 * | 5/2005 | Watari et al. | 250/559.19 |
| 7,064,823 B2 * | 6/2006 | Roche et al. | 356/246 |
| 2004/0076545 A1 * | 4/2004 | Watari et al. | 422/63 |
| 2004/0171102 A1 | 9/2004 | Plank | |
| 2004/0258573 A1 | 12/2004 | Treptow | |
| 2005/0260742 A1 * | 11/2005 | Watanabe | 435/287.3 |

FOREIGN PATENT DOCUMENTS

| | | | |
|---|---|---|---|
| EP | 1 293 782 A2 | 3/2003 | |
| EP | 1498734 A1 * | 1/2005 | |
| EP | 1 873 531 A2 | 1/2008 | |
| JP | 06148202 A * | 5/1994 | |
| JP | 2001074754 A * | 3/2001 | |
| WO | WO 8700086 A1 * | 1/1987 | 422/63 |
| WO | WO 2006068500 A1 * | 6/2006 | |

OTHER PUBLICATIONS

Search Report pertaining to European Patent Application No. 08170322.5 dated Oct. 1, 2009.

* cited by examiner

*Primary Examiner* — Thomas P Noland
(74) *Attorney, Agent, or Firm* — Dinsmore & Shohl LLP (57) ABSTRACT

A method and system for automatically processing of liquid samples involving mixing of the samples with fluids are disclosed. The system includes a storing and handling device for storing and handling of fluid containers, which includes: a storing member provided with a plurality of storing positions, adapted for accommodating the fluid containers, the storing member having at least two storing levels, each of which extending in a plane, which are being stacked in a direction orthogonally aligned to the plane; and a handler, adapted for automatically transferring the fluid containers at least with respect to the storing positions. A method for operating such storing and handling device is also disclosed, wherein individual fluid containers are transferred between storing positions of a same or different storing levels in accordance with processing of the liquid samples.

23 Claims, 7 Drawing Sheets

SYSTEM AND METHOD FOR THE PROCESSING OF LIQUID SAMPLES

TECHNICAL FIELD

Embodiments of the present invention relate to a system and method for the processing of liquid samples involving mixing of the samples with fluids such as reagents as well as a storing and handling device for storing and handling of reagent containers and a method for operating the storing and handling device.

BACKGROUND

In these days, various types of clinical analyzers for automatically analyzing biological liquids such as blood, serum and urine are being in practical use. Analysis of biological liquids basically involves mixing of liquid samples with reagents to allow for chemical or immunochemical reactions for determining presence and amount or absence of specific substances contained in the samples. For example, viral loads may be automatically quantified based on mixing of serum samples with specific reagents, followed by cycling the serum-reagent mixtures obtained through predefined temperature profiles to perform the polymerase chain reaction (PCR).

Since there is a strong demand for offering a wide variety of analytical functions and with a view to improve effectiveness in sample processing, modern analyzers most often process samples in parallel and/or split each sample into a number of aliquots for simultaneous processing thereof deploying different analytical techniques. As a result, due to higher sample throughput and dependent on the number of analytical options offered, modern analyzers are subject to an elevated consumption of reagents which may be satisfied in either preloading the analyzer with an adequate number of reagent containers or performing frequent manual reagent container reloading operations. In the first case, while analyzers can be used in a comfortable stand-alone mode, a larger number of stored reagent containers require much storage space which increases the overall dimensions of the analyzer. In the latter case, while analyzers can be made small and compact, frequent reagent container reloading operations increase the workload on technicians in charge of operating the analyzer, most notably in the event of short time intervals in-between consecutive reloading operations. Moreover, as each reloading operation causes a delay for starting the next run, frequent reloading operations lower effectiveness in sample processing. Even worse, in case the technician fails to reload reagent containers in a timely manner, missing reagents typically cause an interrupt of ongoing runs which may constitute a need to discard the samples currently processed. Some samples, however, are unique in a sense that they can hardly or even not be re-supplied such as in certain forensic cases.

In view of an increasing tendency to install small and compact analyzers to be placed on a laboratory bench or any other suitable surface which enable parallel sample processing and offer a wide variety of analytical options, a convenient trade-off between the number of stored reagent containers and the frequency of manual reloading operations when operating the analyzer in daily routine has to be found. In other words, there is a strong need for preloading (storing) as many reagent containers as possible in an otherwise small and compact analyzer.

In order to keep a comparably large number of reagent containers in readiness for sample analyzing, modern clinical analyzers typically are being provided with supplemental storage space such as supplemental reagent container racks as, for instance, is disclosed in European patent application No. 1498734 A1. This document shows an automatic analyzer including a first storage case storing reagent containers for sample analysis, a supplemental second storage case storing reagent containers for supplemental use and a conveying unit for conveying reagent containers from the second storage case to the first storage case. While the first storage case is a rotatably driven reagent disk, the second storage case may have a box or circular shape and is rotatably driven to place reagent containers in a position facing a reagent container mounting opening used for transferring reagent containers from the first storage case to the second storage case. Hence, while the supplemental second storage case advantageously enables storing of an increased number of reagent containers kept in readiness for transfer to the first storage case for sample analysis, both storage cases require a lot of constructional space which, however, is not in line with the production of small and compact analyzers.

SUMMARY

It is against the above background that embodiments of the invention provide a method and system for the automated processing of liquid samples which, while being compact in overall dimensions, offer a wide variety of analytical options and high-throughput parallel processing of liquid samples without a need to frequently reload fresh reagent containers. Embodiments of the invention also provide a storing and handling device for storing and handling of reagent containers and a method for operating the storing and handling device.

In one embodiment, a system is disclosed for automatically processing of liquid samples involving mixing of the samples with fluids, comprising at least one storing and handling device for storing and handling of fluid containers, which includes: at least one storing member provided with a plurality of storing positions to accommodate the fluid containers, the storing member having at least two storing levels, each of which extending in a plane (X, Y), which are being stacked in a direction (Z) orthogonally aligned to the plane (X, Y), and a handler to automatically transfer the fluid containers at least with respect to the storing positions.

In another embodiment, a modular storing and handling device is disclosed for storing and handling of fluid containers for use in a system for the automated processing of liquid samples involving mixing of the samples with fluids contained in the fluid containers, the storing and handling device comprising: at least one storing member provided with a plurality of storing positions to accommodate the fluid containers, the storing member having at least two storing levels, each of which extending in a plane (X, Y), which are being stacked in a direction (Z) orthogonally aligned to the plane (X, Y); and a handler to automatically transfer the fluid containers at least with respect to the storing positions.

In still another embodiment, a method is disclosed for operating a storing and handling device for storing and handling of fluid containers for use in a system for the automated processing of liquid samples involving mixing of the samples with fluids contained in the fluid containers, the storing and handling device comprising at least one storing member provided with a plurality of storing positions to accommodate the fluid containers, the storing member having at least two storing levels, each of which extending in a plane (X, Y), which are being stacked in a direction (Z) orthogonally aligned to the plane (X, Y), in which the method comprises transferring individual fluid containers between storing positions of a same or different storing levels in accordance with processing of the liquid samples.

Other and further features and advantages of the invention will appear more fully from the following description and claims.

BRIEF DESCRIPTION OF THE DRAWINGS

The accompanying drawings, which are incorporated in and constitute a part of the specification, illustrate various embodiments of the invention, and together with the general description given above and the detailed description given below, serve to explain the principles of the invention, and in which.

REFERENCE LIST

100 System
101 Storing and handling device
102 Reagent container
103 Rack
104 Rear plate
105 Base plate
106 Lower rack level
107 Upper rack level
108 Rack mount
109 Pallet
110 Mount plate
111 Back panel
112 Rib
113 Pallet bottom portion
114 Pallet side wall
115 End surface
116 Abutting surface
117 Handler
118 Positioning device
119 Transfer head
120 Carrier
121 First guiding rail
122 Gear belt
123 First DC electric motor
124 Second guiding rail
125 Spindle
126 Second DC electric motor
127 Gripping mechanism
128 Third DC electric motor
129 Lever mechanism
130 Interstitial space
131 Transfer head mount
132 Head mount side wall
133 Input/output position
134 Reader
135 Compartment
136 Cap
137 Compartment body
138 Hinge portion
139 First-time opener
140 Side wall
141 Lever
142 Lug
143 Top end surface
144 Lever axis
145 Hinged plate
146 Hinge
147 Groove
148 Nipple
149 Pick-up
150 Stirrer
151 Stirrer paddle
152 Fourth DC electric motor
200 System
201 Storing and handling device
202 Reagent container
203 Rack
204 Lower rack level
205 Intermediate rack level
206 Upper rack level
207 Rack mount
208 Pallet
209 Handler
210 Positioning device
211 Transfer head
212 Gripping mechanism
213 Input/output position
214 Compartment
215 Closure
216 Spike
217 Side wall
218 RFID-tag
219 Top end surface
220 Module housing
221 Opening
222 Pipetting device
223 Analyzer components
224 System housing
225 Upper wall
226 Holes

DETAILED DESCRIPTION

According to a first aspect, an embodiment of the invention provides a new system for the automated processing of liquid samples basically involving mixing of the samples with fluids such as reagents. The system comprises at least one storing and handling device for storing and handling of fluid containers containing fluids such as reagents for mixing with the liquid samples. The storing and handling device may be configured as an integrated system component of the system for the automated processing of liquid samples. It may also be configured as a modular system component of the system for the automated processing of liquid samples which, for instance, advantageously enables the storing and handling device to be readily adapted to various system sizes. In that, the modular storing and handling device may be accommodated by a module housing.

The storing and handling device includes at least one storing member having a plurality of storing positions, adapted for storing the fluid containers (e.g. reagent containers). Specifically, the storing member is provided with at least two storing levels, each of which extending in a plane spanned in first and second directions, with the first direction being orthogonally aligned to the second direction, which levels are stacked in a third direction, with the third direction being orthogonally aligned to the plane, that is to say, to both first and second directions. The storing levels may, for instance, extend in horizontal planes and be stacked in vertical relationship with respect to each other.

Each of the storing levels is adapted to store a plurality of one- or two-dimensionally arrayed fluid containers. Accordingly, the fluid containers may be serially arranged with respect to each other, for instance aligned along the first direction to form a (e.g. horizontal) row of fluid containers, or, may be serially arranged with respect to each other in each of a plurality of (e.g. horizontal) rows, for instance, extending along the first direction, with the rows being arranged in the second direction.

The storing and handling device further includes a handler which is adapted to automatically handle (manipulate) fluid containers, in particular, with respect to the storing positions, so that each fluid container may be transferred from one storing position to another storing position.

The system may further comprise a controller for controlling of processing of the samples including control of the storing and handling device.

Accordingly, due to a highly-dense packaging of the fluid containers as above-detailed, the system of the invention may advantageously be made compact in dimensions without requiring frequent reloading operations for refilling of fresh fluid containers even in case of a comparably high consumption of fluids in processing the liquid samples.

According to a preferred embodiment of the system of the invention, the storing and handling device has a function of cold-storage, that is to say, is operable to cool the fluid containers in their storage positions. Due to the highly-dense packaging of the fluid containers, efficient cooling of the fluid containers may advantageously be performed.

According to another preferred embodiment of the system of the invention, the storing member is provided with a plurality of mounts, each of which being adapted to detachably support a supporting member such as a pallet for supporting of at least one fluid container. Such embodiment advantageously allows individual supporting members to be inserted in the storing member or removed therefrom, so that the supporting members may be transferred from one storing position to another storing position, thus advantageously allowing individual fluid containers to vary in size and shape without requiring specific adaptations of the storing positions.

According to yet another preferred embodiment of the system of the invention, the system includes at least one first-time opener such as a hinged lever or spike, adapted for initial opening of at least one fluid container, wherein operation of the first-time opener to initially open the fluid container preferably is coupled with moving the fluid container and/or first-time opener by means of the handler so that no additional components such as drives or positioning devices are required.

According to yet another preferred embodiment of the system of the invention, the system further includes one or more devices, the operation of each of which preferably is coupled to moving of at least one fluid container and/or the device by means of the handler, which are selected from the group of devices consisting of:

(a) an opener/closer, adapted for raising or lowering a cap of at least one fluid container provided with a hinged cap reversibly fixable to a container body;
(b) a stirrer, adapted for stiffing a fluid contained in a fluid container;
(c) a reader, adapted for reading machine-readable information (e.g. contained in a barcode label and/or RFID-tag) which at least one fluid container is provided with;
(d) a shaker, adapted for shaking of fluids such as magnetically attractable particles contained in the fluid containers; and
(e) a washer, adapted for washing the stirrer.

Since the handler is used for selectively moving the fluid containers, operation of above devices may advantageously be performed without requiring additional drives or positioning devices.

According to yet another preferred embodiment of the system of the invention, the system further includes at least one input/output position (e.g. input/output station), adapted for loading/removing of fluid containers to/from the system which advantageously allows for manual or automated loading and/or unloading operations without a need to stop running liquid sample processing.

According to yet another preferred embodiment of the system of the invention, the storing and handling device includes two storing members respectively being provided with storing positions for storing of fluid containers arranged in opposite relationship with respect to each other, with the handler being arranged in-between the storing members for automatically transferring the fluid containers, in particular, with respect to the storing positions of both storing members. Such embodiment advantageously allows for a particularly highly-dense packaging of fluid containers without a need to provide for individual handlers for handling the fluid containers which advantageously allows for saving constructional space and costs.

According to yet another preferred embodiment of the system of the invention, the storing member is provided with at least one storing position, adapted for pipetting of fluids contained in at least one fluid container stored therein, in the following referred as "pipetting position". It may be preferred that the at least one pipetting position is located in an uppermost storing level of the storing member. Accordingly, since pipetting of fluids may be performed in storing positions, a risk of spilling and/or contamination of fluids when transferring fluid containers to pipetting positions other than the storing positions may advantageously be avoided. Moreover, since the fluid containers may be continuously cooled in pipetting positions, cooling of the fluids is enabled even during and in-between pipetting operations, so that deterioration of fluids may be inhibited in a highly efficient manner to thereby increase reliability of the system.

In above embodiment of the invention, it may be preferred that the system further comprises at least one pipetting device including at least one pipette provided with a disposable or re-usable pipette tip, adapted to transfer fluids contained in fluid containers stored in the pipetting positions to the liquid samples.

According to yet another preferred embodiment of the system of the invention, the storing member for storing of the fluid containers is made up of plural modular storing sub-members which may be added to or removed from the storing member. Such embodiment advantageously allows for readily adapting the size of the storing member to specific needs of the user and/or the size of the system. Specifically, individual storing sub-members may be removed from the storing member for fluid container loading/unloading operations or fluid container cooling in placing the storing sub-members in a cooling device located outside the system. Individual storing sub-members may, for instance, correspond to the storing levels of the storing member.

According to a second aspect, an embodiment of the invention provides a new modular storing and handling device for storing and handling of fluid containers for use in a system for the automated processing of liquid samples involving mixing of the samples with fluids such as reagents. The modular storing and handling device comprises at least one storing member having a plurality of storing positions for storing of the fluid containers (e.g. reagent containers). The storing member is provided with at least two storing levels, each of which extending in a plane spanned in first and second directions, with the first direction being orthogonally aligned to the second direction, which storing levels are stacked in a third direction, with the third direction being orthogonally aligned to the plane. The storing and handling device further includes a handler, adapted to automatically transfer the fluid containers with respect to the storing positions.

According to a third aspect, another embodiment of the invention provides a method for operating a storing and handling device provided with storing positions for storing of fluid containers of a system for the automated processing of liquid samples involving mixing of the samples with fluids contained in the fluid containers, wherein the storing and handling device is provided with at least two storing levels, each of which extending in a plane, which are stacked in a direction vertical to the plane. The method includes a step of selectively transferring at least one fluid container from one storing position to another storing position of a same or different storing levels in accordance with processing of the liquid samples.

According to a preferred embodiment of the method of the invention, it includes a step of selectively transferring at least one fluid container to a storing position, preferably located at an uppermost storing level, adapted for pipetting of fluids contained in the fluid container in accordance with processing of the liquid samples.

According to another preferred embodiment of the method of the invention, one or more steps selected from the following group of steps are performed, which group consists of:
(a) initially opening of at least one fluid container;
(b) raising/lowering of at least one hinged cap of at least one of the fluid containers;
(c) stirring of the fluid contained in at least fluid container;
(d) washing of a stirrer;
(e) shaking of at least one fluid container for mixing of the fluid contained therein; and
(f) reading of at least one machine-readable information which at least one fluid container is labelled with.

According to a fourth aspect, still another embodiment of the invention provides a method for operating a system for the automated processing of liquid samples involving mixing of the samples with fluids contained in the fluid containers comprising a method for operating the storing and handling device as above-described.

The above embodiments of the present invention will now be described in detail below with reference to the accompanying drawings, where like designations denote like or similar elements.

With particular reference to FIGS. 1 through 4, an exemplary first embodiment of the system of the invention including a first embodiment of the storing and handling device for storing and handling of reagent containers is explained.

In the following description, reference is made to first to third directions which are orthogonally oriented with respect to each other (X-, Y-, Z-direction), wherein, without imposing any limitation to the invention, the first and second directions (X-, Y-direction) are assumed to span a horizontal plane with the third direction (Z-direction) being vertically aligned.

Figure 1:
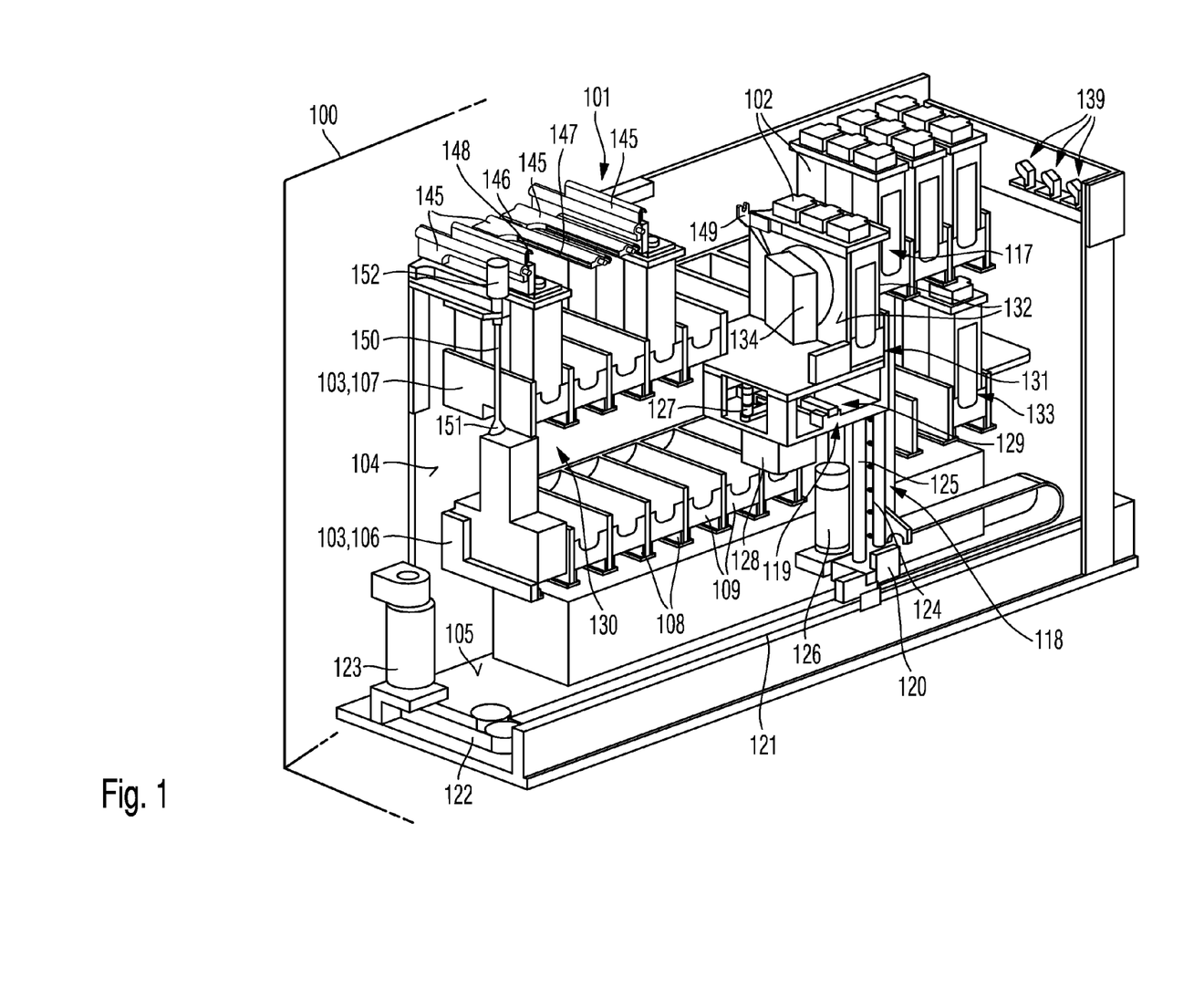
FIG. 1 is an elevational view of an exemplary embodiment of the system of the invention comprising a first embodiment of the storing and handling device.

Accordingly, a system 100 for the processing of liquid samples involving mixing of the liquid samples with specific reagents contained in reagent containers to initiate chemical or immunochemical reactions in the sample-reagent mixtures obtained is disclosed. Liquid samples to be used in liquid processing may include biological fluids (e.g. blood, serum, urine, cerebrospinal fluids and nucleic acids (DNA/RNA) containing fluids), non-biological fluids (e.g. chemical compounds and drugs) and any other fluid of interest as long as processing thereof involves mixing with reagents. The system 100 for the processing of liquid samples may, for instance, be embodied as clinical analyzer (e.g. chemical and/or immunochemical analyzer) for analyzing of liquid samples in order to determine presence/amount or absence of specific substances in the liquid samples.

The system 100 for the processing of liquid samples includes at least one storing and handling device 101 for storing plural reagent containers 102 containing reagents to be mixed with the liquid samples for the processing thereof. The storing and handling device 101 can be considered a functional entity which may be embodied as a modular or integrated system component of the system 100.

The storing and handling device 101 is provided with a rack 103 (in the introductory portion called storing member) which, for instance, is fixed to a vertical rear plate 104 supported by horizontal base plate 105. The rack 103 is provided with two separate rack levels 106, 107 which are positioned one upon the other in vertical Z-direction, in the following identified as lower rack level 106 and upper rack level 107. Each rack level 106, 107 is a modular rack component which, for instance, is detachably fixed to the rear plate 104, enabling each of the individual rack levels 106, 107 to be added to or removed from the rack 103 as desired.

Each rack level 106, 107 is provided with a plurality of box-like rack mounts 108 for accommodating of pallets 109 for supporting the reagent containers 102, which are serially arranged with respect to each other in horizontal Y-direction. Each rack level 106, 107 includes a plurality of vertical mount plates 110 extending in horizontal X-direction which are serially arranged with respect to each other in horizontal Y-direction and a vertical back panel 111 extending in horizontal Y-direction which is connected to the vertical mount plates 110 at rear plate 104 oriented vertical end faces thereof. Each pair of adjacent mount plates 110 together with the back panel 111 serve as side and back walls, respectively, to mutually frame an individual box-like rack mount 108.

Each mount plate 110 serving as rack mount 108 side wall is provided with a rib 112 formed at the lower horizontal end face thereof extending in horizontal X-direction. While not shown in the figures, the back panel 111 serving as rack mount 108 back wall may also be provided with a rib formed at the lower horizontal end face thereof extending in horizontal Y-direction.

In the storing and handling device 101 of the system 100, the reagent containers 102 are supported by the pallets 109 (in the introductory portion called supporting members), each of which having a pallet bottom portion 113 for supporting the reagent container 102 and two pallet side walls 114 sandwiching the reagent container 102 in-between to keep it in an upright position.

Figure 2A:
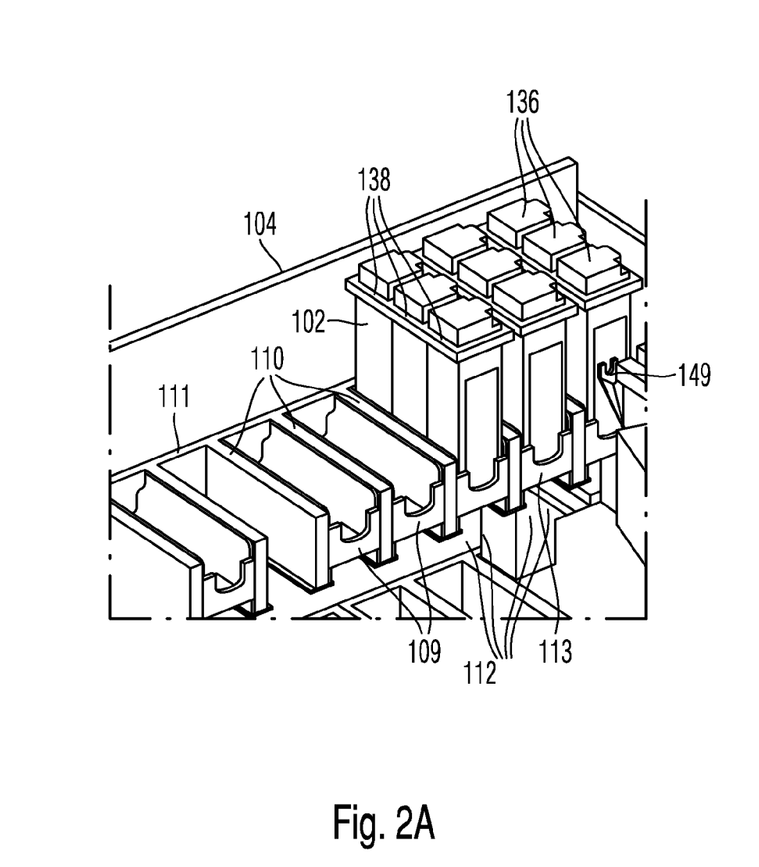
FIGS. 2A-2B are elevational partial views of the storing and handling device of FIG. 1 illustrating inserting/removing of the pallets.
Figure 2B:
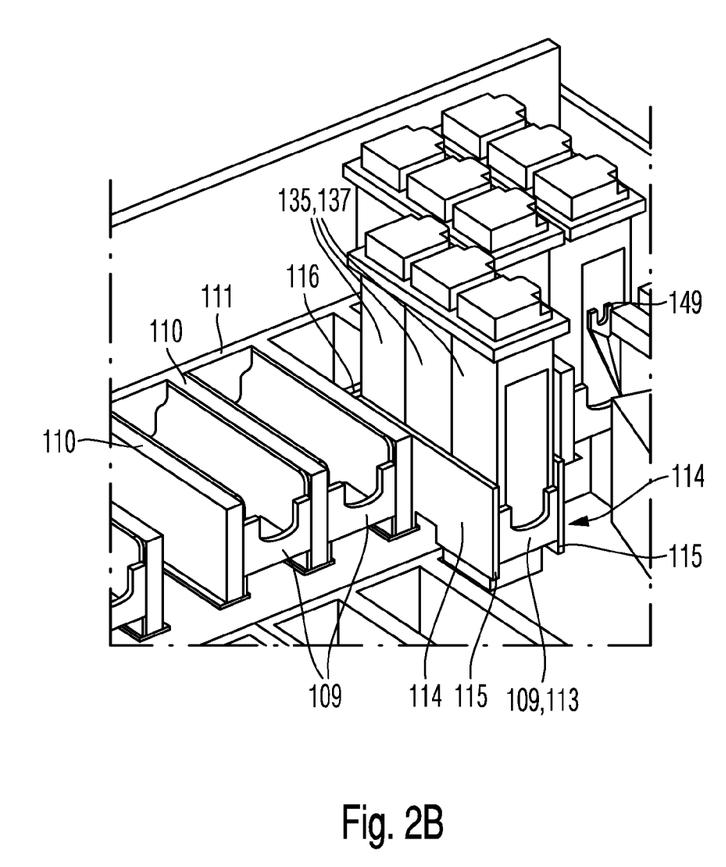

Each pair of adjacent vertical mount plates 110 framing a rack mount 108 enables insertion of an individual pallet 109, with the rack mounts 108 being adapted to slidably support the pallets 109 based on a dedicated sliding mechanism. As illustrated in FIGS. 2A and 2B, when inserting an individual pallet 109 in a rack mount 108, lower end surfaces 115 of the pallet side walls 114 get into sliding engagement with the ribs 112 formed by the mount plates 110, so that the pallet 109 can be slidably moved along the horizontal X-direction towards the rear plate 104 until a vertical abutting surface 116 of the pallet bottom portion 113 abuts against the back panel 111 of the rack mount 108. On the other hand, each pallet 109 can be slidably moved away from the rear plate 104 to remove the pallet 109 from the rack 103. Each pallet 109, when accommodated in a rack mount 108 identifies a storing position for storing the reagent container 102 supported by the pallet 109.

While not shown in the figures, each of the ribs 112 supporting the pallets 109 may be provided with a (e.g. semicircular) projection such as a cam extending in vertical Z-direction which, in case the pallets 109 are fully inserted in the rack mount 108, get into fitting engagement with recesses formed in the horizontal end surfaces 115 of the pallet side walls 114, so that the pallets 109 are secured in storing positions to hinder unintended loosening of the pallets 109 in case of vibrations or the like.

The storing and handling device 101 of the system 100 further includes a handler 117 for handling (manipulating) the reagent containers 102 with respect to the storing positions. The handler 117 is provided with a positioning device 118 for positioning of a transfer head 119 along two directions of travel (Y-direction and Z-direction) by means of a two-rail translation mechanism. Stated more particularly, the positioning device 118 includes a carrier 120 supporting the transfer head 119 which is slidably supported by a first guiding rail 121 extending along the horizontal Y-direction. Driven by means of a gear belt drive including gear belt 122 and first DC electric motor 123, the carrier 120 can be freely moved along the first guiding rail 121 to position the transfer head 119 along horizontal Y-direction. The positioning device 118 further includes a second guiding rail 124 extending along the vertical Z-direction which slidably supports the transfer head 119. Driven by means of a spindle drive including spindle 125 and second DC electric motor 126, the transfer head 119 can be freely moved in vertical Z-direction to increase or decrease a distance between the transfer head 119 and the carrier 120. Based on the two-rail translation mechanism, the transfer head 119 may be freely moved in a vertical Y-Z-plane to selectively face each one of the reagent containers 102.

The transfer head 119 is provided with a gripping mechanism 127 for gripping of individual reagent containers 102 by means of a gripping pin (not illustrated). Driven by a third DC electric motor 128, the gripping pin may be freely moved in a horizontal X-Y-plane by means of a lever mechanism 129 which is not further detailed herein. In particular, the gripping pin can be moved towards and away from the rear plate 104 to dip into an interstitial space 130 in-between both rack levels 106, 107 for loading/unloading of individual pallets 109 to/from the rack mounts 108. For this purpose, the gripping pin may for instance be brought into fitting engagement with an undercut recess formed in a bottom-side end surface of the pallet bottom portion 113 of each of the pallets 109, which is well-known to those of skill in the art and therefore need not be further detailed herein.

Having gripped an individual pallet 109 by means of the gripping mechanism 127 as above-detailed, the pallet 109 (with or without reagent container 102) may be drawn onto the transfer head 119 which is provided with a transfer head mount 131 adapted for accommodating the pallet 109. The transfer head mount 131 includes two vertical head mount side walls 132 which are provided with ribs (not detailed in the figures) extending in horizontal X-direction for slidably supporting the pallet side walls 114 similarly to the rack mounts 108. The head mount side walls 132 keep the reagent container 102 supported by the pallet 109 in an upright position.

Vertically arraying the pallets 109 in a two-level rack 103 enables free access (i.e. random access) to the reagent containers 102 stored therein, so that the reagent containers 102 may be arbitrarily placed in any storing position as defined by the rack mounts 111 or removed therefrom by means of the handler 117. Moreover, a highly-dense packaging of reagent containers 102 is being realized, in which voids in-between adjacent reagent containers 102 can be made small or may even disappear as long as frictional forces allow for slidably moving the pallets 109 with respect to their storing positions. Similarly, the interstitial space 130 between both rack levels 106, 107 may be made small in appropriately choosing a vertical distance between the rack mounts 108 in accordance with a vertical height of the reagent containers 102.

In the system 100 for processing of liquid samples, the storing and handling device 101 may be operated as cold-storage for cooling of the stored reagent containers 102, wherein cooling of reagent containers 102 may, for instance, be performed by circulating cooling-air. Due to the highly-dense packaging of the reagent containers 102, cooling of the reagent containers 102 can be highly efficiently performed.

The storing and handling device 101 of the system 100 further includes at least one input/output position 133 which, being similar in construction to the storing positions for storing of the reagent containers 102 thus enabling manipulation of reagent containers 102 using the handler 117, allows for a manual or automated loading/unloading of reagent containers 102 when performing processing of the liquid samples.

In the storing and handling device 101 of system 100, each reagent container 102 may bear a machine-readable label (not shown in the figures) which can be automatically read by a reader 134 for reading of machine-readable information which, for instance, is in the form of a barcode carried by a label which is positioned on a handler 117 facing side of the reagent containers 102. The information carried in machine-readable form on the label identifies individual reagent containers 102 and may, for instance, code for a lot number or any other information suitable for identifying reagent containers 102. It may also contain additional information such as use-by date which may be relevant for use of the reagents contained. Fixed to the transfer head 119, the reader 134 may be moved in a position selectively facing a machine-readable label of each of the reagent containers 102 stored in the rack 103.

Each reagent container 102 includes three separate (reagent) compartments 135 arranged in serial alignment with respect to each other which may contain same or different reagents in accordance with specific demands for the processing of liquid samples. The reagent containers 102 may, for instance, be embodied as reagent kits containing reagents required for selectively performing a specific analytical function. It goes without saying that individual reagent containers 102 may include a larger or smaller number of compartments 135 as appropriate. Each compartment 135 is provided with a cap 136 pivotably attached to a three-cavity forming (common) compartment body 137 at a hinge portion 138. Since fresh reagent containers 102 usually are being sealed, they must be brake open when opening the compartments 135 for the first time. After breaking open, the hinged cap 136 can be reversibly raised from or lowered to the compartment body 137 to be at least partially closed.

Figure 3:
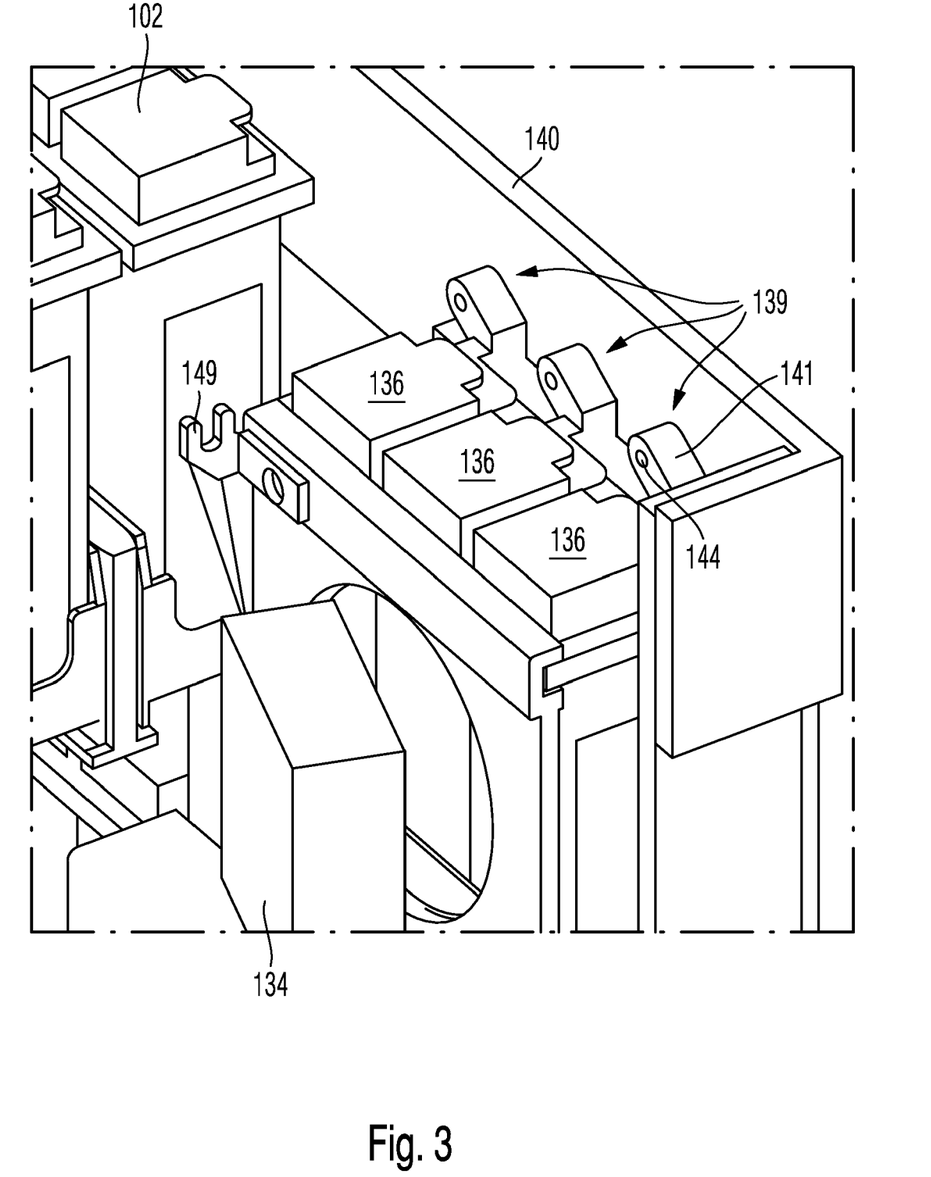
FIG. 3 is another elevational partial view of the storing and handling device of FIG. 1 illustrating the first-time openers.

The storing and handling device 101 of the system 100 further includes three first-time openers 139 for initially opening (breaking-open) the compartments 135 of individual reagent containers 102. The first time openers 139 are attached to a vertical side wall 140 of the storing and handling device 101 serially arranged with respect to each other in horizontal X-direction to be freely accessible by a handler 117 moved reagent container 102.

Figure 4A:
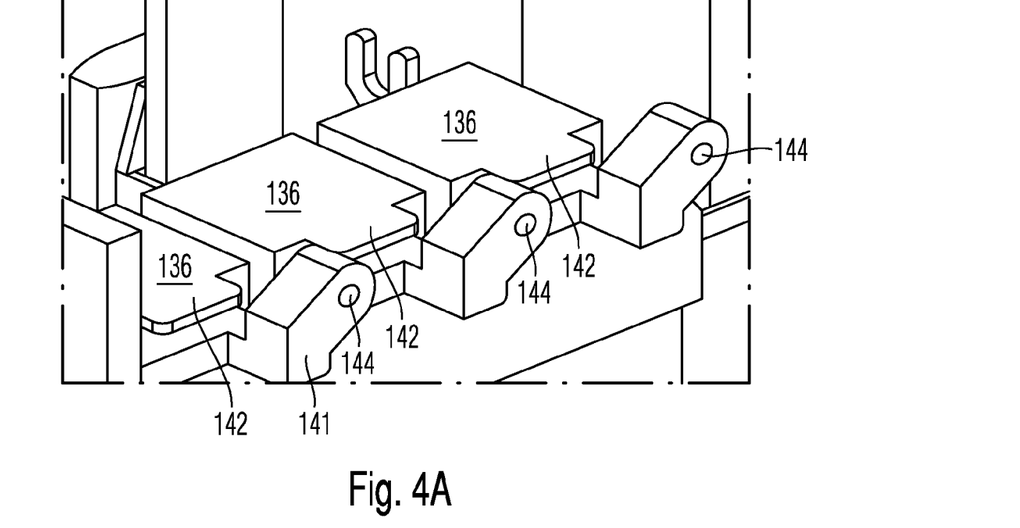
FIGS. 4A-4B are elevational partial views illustrating operation of the first-time openers of FIG. 3.
Figure 4B:
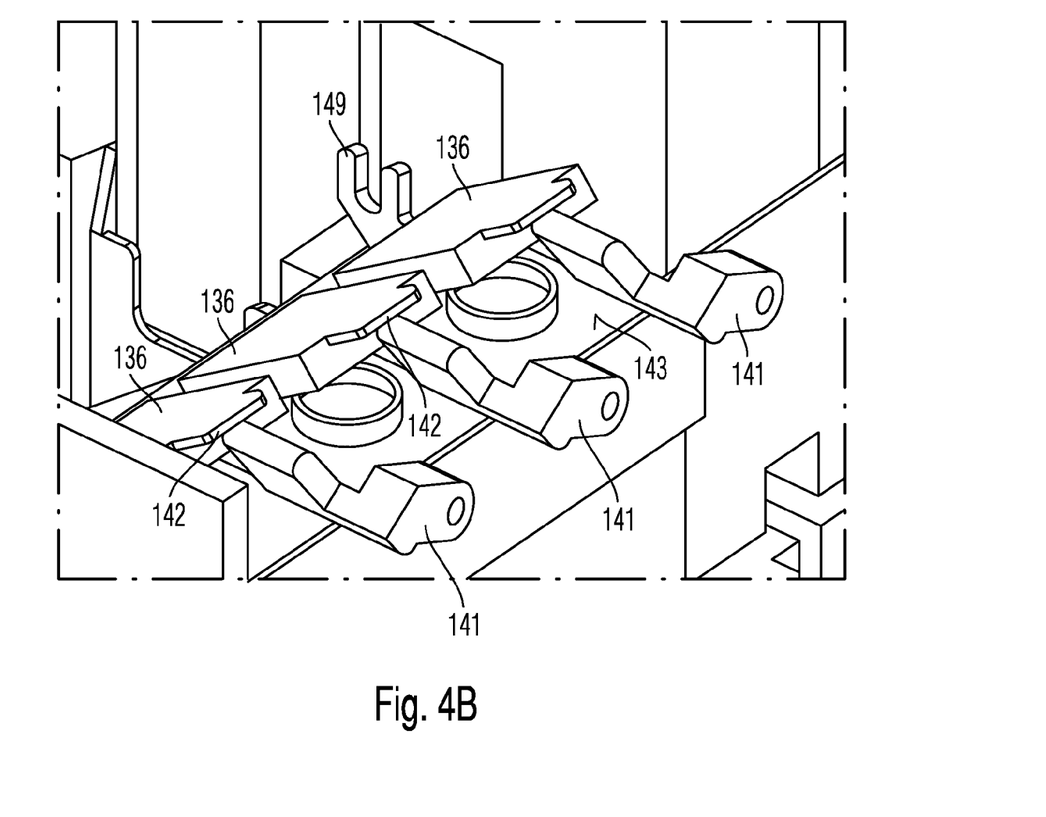

As illustrated in FIGS. 4A and 4B, when opening the reagent container 102 compartments 135 for the first time, the reagent container 102 concerned is gripped by the handler 117 and positioned in such a way that a lever 141 of each of the first-time openers 139 can penetrate into an interstitial space between a cap 136 projecting lug 142 and a top end surface 143 of the compartment body 137. When performing an upwards movement along Z-direction, each lever 141 is rotated around lever axis 144 which results in raising the caps 136 from the compartment body 137 to break the compartments 135 open. When the reagent container 102 is removed from the first-time openers 139, due to a spring force respectively biasing each of the levers 141, the levers 141 return to starting positions as illustrated in FIG. 4A.

While not shown in the figures, the storing and handling device 101 of the system 100 may further include an opening and closing device such as a horizontal bar which being arranged to be freely accessible by a handler 117 moved reagent container 102 may be used for raising or lowering of the caps 136 with respect to the compartment body 137 when positioning the bar at the caps 136 and performing an upwards or downwards movement of the reagent container 102 by means of the handler 117.

While not shown in the figures, the system 100 for processing of liquid samples may further include at least one pipetting device including at least one pipette provided with a disposable pipette tip or re-usable pipette needle to transfer fluids to or from the compartments 135 of the reagent containers 102 when stored in dedicated storing positions, which preferably are being located in the upper rack level 107 of the rack 103.

As illustrated in FIG. 1, the storing and handling device 101 is provided with at least one (e.g. four) pipetting position, that is to say, storing positions adapted for pipetting of reagents, in the upper rack level 107 of the rack 103 which can be used for pipetting of reagents contained in the compartments 135 of the reagent containers 102 accommodated therein. In FIG. 1, pipetting positions of the upper rack level 107 are indicated by four hinged plates 145 which, due to linkage to the rear plate 104 by hinges 146, may be rotated around axes extending in X-direction. More specifically, each of the hinged plates 145 is provided with a groove 147 extending in horizontal X-direction which, when inserting a pallet 109 supporting a reagent container 102 into the rack mount 108, gets into fitting engagement with the cap 136 projecting lugs 142 of each of the compartments 135 of the reagent container 102. Each hinged plate 145 is further provided with a nipple 148 projecting in the X-direction which can be operated to rotate the hinged plate 145 to raise or lower the caps 136 with respect to the compartment body 137 by means of a pick-up 149 fixed to the transfer head 119 of the handler 117. Accordingly, compartments 135 of each of the reagent containers 102 can be selectively opened or closed (after initial breaking-open) as desired using the handler 117 when storing the reagent container 102 in pipetting position.

Furthermore, the storing and handling device 101 is provided with a stirrer 150 for stirring of reagents contained in the compartments 135 of the reagent containers 102. More specifically, in order to stir reagents, the handler 117 is used for moving a reagent container 102 in a position that stirrer paddle 151 can dip into a compartment 135 for stirring of the reagent contained therein. The stirrer 150 is driven by fourth DC electric motor 152.

Figure 5:
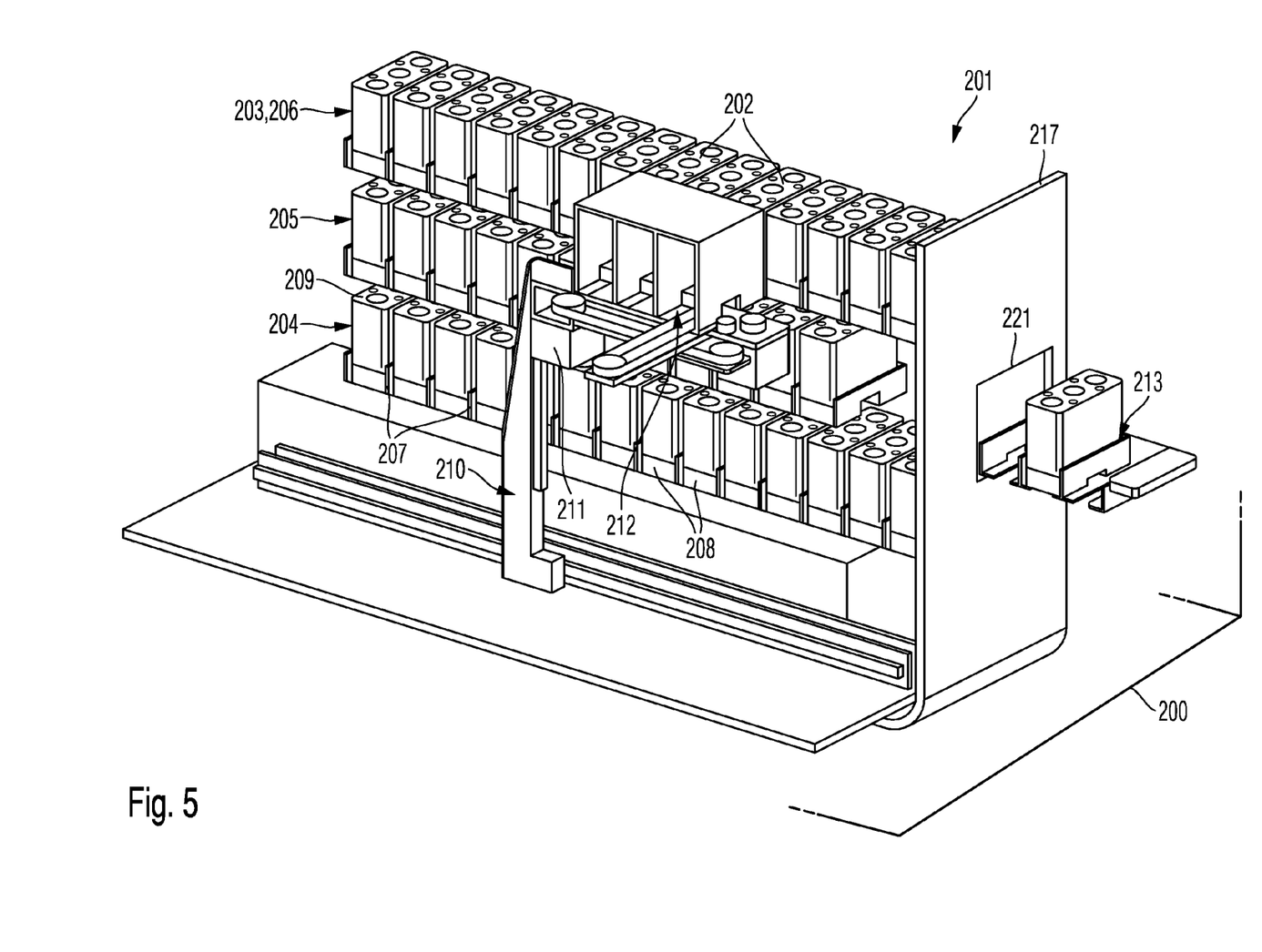
FIG. 5 is an elevational partial view of another exemplary embodiment of the system of the invention comprising a second embodiment of the storing and handling device.
Figure 6:
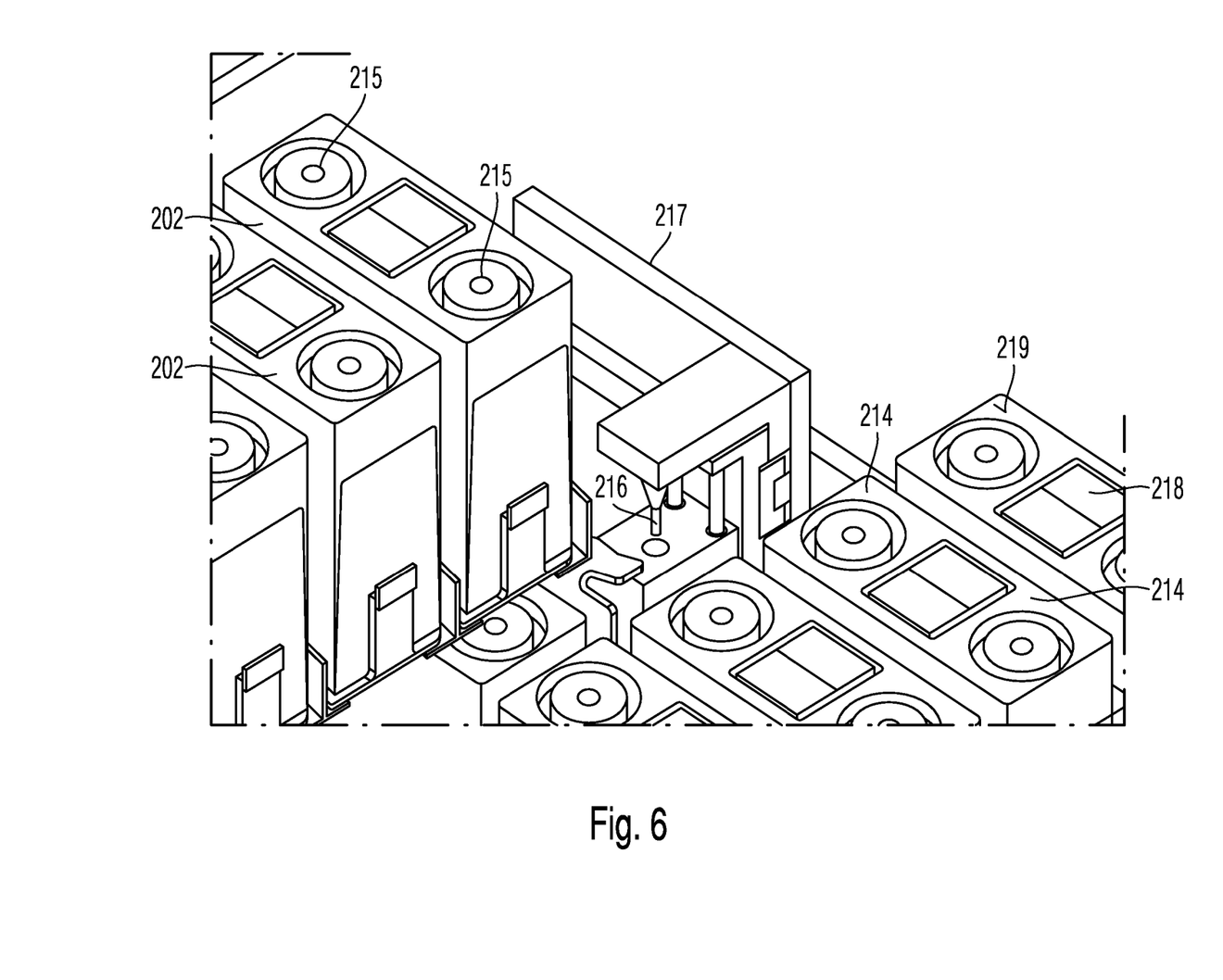
FIG. 6 is an elevational partial view of the system of FIG. 5 illustrating another first-time opener.

Reference is now made to FIGS. 5 to 6 illustrating a second embodiment of the system for processing of liquid samples including a second embodiment of the storing and handling device for storing of reagent containers. In order to avoid unnecessary repetitions, only differences with respect to the first embodiment of invention are explained and otherwise reference is made to explanations made above in connection with FIGS. 1 through 4.

Accordingly, a system 200 for the processing of liquid samples which includes at least one storing and handling device 201 for storing plural reagent containers 202 containing reagents to be mixed with the liquid samples for the processing thereof. The storing and handling device 201 is a modular or integrated system component of the system 200.

The storing and handling device 201 includes a rack 203 provided with three separate rack levels 204-206 which are positioned one upon the other in vertical Z-direction, in the following identified as lower rack level 204, intermediate rack level 205 and upper rack level 206. Each rack level 204-206 is a modular rack component which may be added to or removed from the rack 203. The rack levels 204-206 are provided with a plurality of box-like rack mounts 207 for accommodating of pallets 208 identifying storing position for storing the reagent containers 202. Individual pallets 208 may be inserted in or removed from the rack mounts 207 as desired.

The storing and handling device 201 of the system 200 includes a handler 209 for handling (manipulating) the reagent containers 202 with respect to the storing positions. The handler 209 is provided with a positioning device 210 for positioning of a transfer head 211 along two directions of travel (Y-direction and Z-direction) by means of a two-rail translation mechanism.

The transfer head 211 is provided with a gripping mechanism 212 (not detailed in the figures) including a gripping pin for gripping of individual reagent containers 202 which can be moved towards and away from the reagent containers 202 stored in the rack 203. Having gripped an individual pallet 208, the pallet 208 may be drawn onto the transfer head 211 which is provided with three transfer head mounts 213, each of which being adapted for accommodating the pallets 208. The gripping pin for gripping of reagent containers 202 may be moved to each of the transfer head mounts 213 for inserting/removing individual reagent containers 202 (not detailed in the figures). Hence, up to three reagent containers 202 may be simultaneously loaded onto the transfer head 211 which may be commonly transferred, in particular, with respect to the storing positions.

Vertically arraying the pallets 208 in a three-level rack 203 enables free access to the reagent containers 202 stored therein, so that the reagent containers 202 may be arbitrarily placed in any storing position as defined by the rack mounts 207 or removed therefrom by means of the handler 209.

The storing and handling device 201 of the system 200 includes at least one input/output position 213 which, being similar in construction to the storing positions for storing of the reagent containers 202 enabling manipulation of reagent containers 202 using the handler 209, allows for a manual or automated loading/unloading of reagent containers 202 when performing processing of the liquid samples. The input/output position 213 is slidably supported by the storing and handling device 201 so that it may be readily inserted in or removed from the storing and handling device 201 through opening 221 of the side wall 217.

Each reagent container 202 includes two separate (reagent) compartments 214 which may contain same or different reagents in accordance with specific demands for the processing of liquid samples, each of which being provided with a pre-punched closure 215.

As illustrated in FIG. 6, the storing and handling device 201 of the system 200 further includes a spike 216 for initially opening (breaking-open) the compartments 214 of individual reagent containers 202. The spike 216 is attached to a vertical side wall 217 of the storing and handling device 201 to be freely accessible by a handler 209 moved reagent container 202. For opening the reagent container 202 compartments 214 for the first time, the reagent container 202 concerned is gripped by the handler 209 and, following positioning the closure 215 of individual compartments 214 under spike 216, is moved upwards so that the spike 216 may penetrate the closure 215.

In the storing and handling device 201 of system 200, each reagent container 202 bears a machine-readable label in the form of a RFID-tag 218 (RFID=radio frequency identification) positioned on a top end surface 219 thereof containing information with respect to the reagent container 202 which can be read by a RFID-reader (not illustrated) which, for instance, is attached to the side wall 217 neighbouring input/output position 213.

Figure 7:
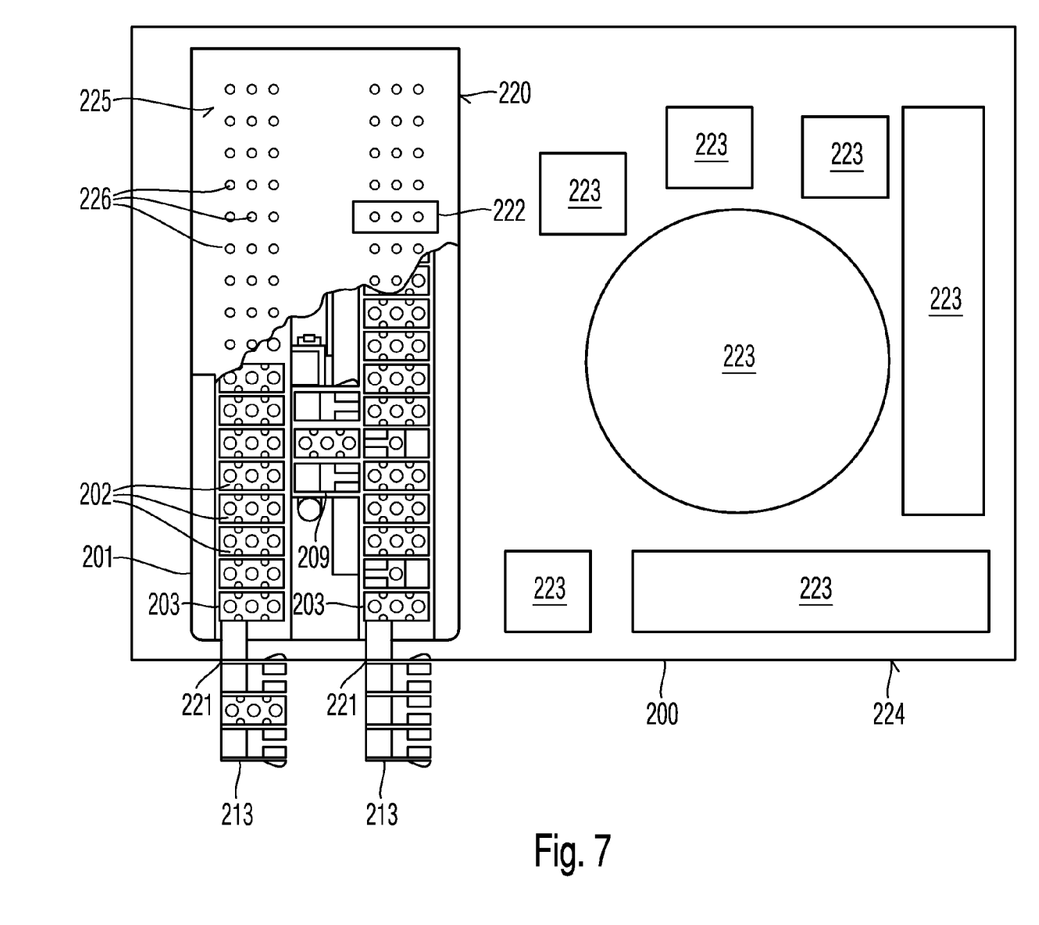
FIG. 7 is an elevational view of a variant of the system of FIG. 5.

Reference is made to FIG. 7 illustrating a variant of the system 200 of FIGS. 5 and 6. The system 200 which embodies an analyzer, e.g. a clinical analyzer, includes a modular storing and handling device 201 accommodated in a module housing 220 and various analyzer components 223 not belonging to the storing and handling device 201 which are not further detailed herein.

The storing and handling device 201 has two separate racks 203, each of which being provided with three separate rack levels as illustrated in FIG. 5. It further includes a handler 209 as illustrated in FIG. 5 positioned in-between both racks 203 for handling (manipulating) the reagent containers 202 with respect to the storing positions of both racks. It yet further includes a pipetting device 222 to transfer fluids to or from the compartments of the reagent containers 202 when stored in dedicated storing positions, which preferably are being located in the uppermost rack levels of the racks 203. The reagent containers 202 remain in the storing and handling device 201 during pipetting. Access to the reagent containers 202 is provided through holes 226 in the upper wall 225 of the module housing 220.

Both racks input/output positions 213 (input/output stations) are slidably supported by the storing and handling device 201 (which is not further detailed in FIG. 7), so that each input/output position 213 may be readily inserted in or removed from the storing and handling device 201 through opening 221 of system housing 224.

In the systems 100, 200 for the processing of liquid samples as above-described, a controller (not shown in the figures) is used for controlling of liquid processing including handling of reagent containers 102, 202 by means of the handler 117, 209. The controller may, e.g., be embodied as a programmable logic controller running a machine-readable program provided with instructions to perform operations in accordance with a predetermined process operation plan for processing of the liquid samples. In that, the controller is electrically connected to the system components which require control, so that the controller is enabled to receive information from the different system components and to transmit corresponding control signals for controlling the components according to the process operation plan, particularly including the handler 117, 209 for transferring the reagent containers with respect to the storing positions of the rack 103, 203 as well as input/output positions 133, 213.

Stated more particularly, in the system 100, 200 for processing of liquid samples, individual reagent containers 102, 202 can be transferred in-between a same rack level and/or different rack levels 106-107, 204-206 by means of the handler 117, 209 as required in accordance with processing of the liquid samples. Individual reagent containers 102, 202 can, for instance, be transferred from a lower rack level 106, 204-205 to a pipetting position (storing position, adapted for pipetting of reagents) preferably located at the uppermost rack level 107, 206 to enable pipetting of reagents contained in the reagent containers 102, 202 for processing of the liquid samples by means of the pipetting device. Otherwise, in case reagents are no longer needed for the processing of liquid samples, the reagents containers 102, 202 concerned can be transferred from the pipetting positions to each one of the lower rack levels for later usage. Stated more generally, individual reagent containers 102, 202 can be arbitrarily transferred in-between each rack level and/or from one rack level to another rack level to thereby perform an automated warehousing of the reagent containers 102, 202 stored. Most advantageously, input/output positions 133, 213 may be used to manually or automatically load/unload reagent containers 102, 202 into/from the system 100, 200 without a need to interrupt an ongoing run when processing liquid samples. In advance to using reagents for the processing of liquid samples, each compartment 135, 214 of the reagent containers 102, 202 can be automatically first-time opened using a first time opener 139, 216, the operation of which is coupled to appropriately moving each of the reagent containers 102, 202 by the handler. When using reagent containers 102 having a snap-fit closable cap 136, automated opening and closing, i.e. raising and lowering of the cap 136 with respect to the compartment body 137, may be performed, for instance, using hinged plates 145. Reagents contained in the reagent containers 102, 202 can be automatically stirred using a stirrer 150 so that, for instance, suspensions of magnetically attractable particles may be re-suspended when appropriate. Also, washing of the stirrer may automatically be performed using a washing device so that contamination of reagents may be avoided. Labelling the reagent containers 102, 202 by labels such as RFID-tags 218 containing machine-readable information combined with automatically reading the information by a reader allows for an identification of reagents prior to use in processing of liquid samples. Selectively adding/removing of storing sub-members such as rack levels, advantageously allows for readily varying the size of the rack 103, 203 as appropriate. Moreover, individual storing sub-members may be transferred to a cooling device located outside the system 100, 200 for cooling of the reagent containers 102, 202 stored and replaced when appropriate.

Moreover, in each of the systems 100, 200, two racks 103, 203 may be arranged in opposite relationship with respect to each other, with a single handler 117, 209 arranged in-between the racks to selectively manipulate the reagent containers 102, 202 at least with respect to the storing positions (as illustrated in FIG. 7).

Hence, the embodiments of the present invention circumvent the problems of prior art in providing an improved system for the automated processing of liquid samples which, even in case of a comparably high consumption of reagents, due to a highly-dense packaging of reagent containers, can be made compact without requiring frequent reagent container refilling operations. Furthermore, due to the highly-dense packaging of reagent containers, efficient cooling thereof may be performed. The storing and handling device is readily scalable with respect to the number of reagent containers stored, so that it may be readily adapted to differently sized systems for the processing of liquid samples. On the other hand, the storing and handling device may be readily downscaled or up-scaled with respect to the number of reagent containers stored according to specific demands of users.

Therefore, in one preferred embodiment a system 100, 200 is provided for automatically processing of liquid samples involving mixing of the samples with fluids. The system 100, 200 comprises at least one storing and handling device 101, 201 for storing and handling of fluid containers 102, 202, including: at least one storing member 103, 203 provided with a plurality of storing positions 108, 207, adapted for accommodating the fluid containers 102, 202, the storing member 103, 203 having at least two storing levels 106-107, 204-206, each of which extending in a plane X, Y, which are being stacked in a direction Z orthogonally aligned to the plane X, Y; and a handler 117, 209, adapted for automatically transferring the fluid containers 102, 202 at least with respect to the storing positions 108, 207.

In another embodiment, the storing and handling device 101, 201 is operable to cool the fluid containers 102, 202.

In another embodiment, the storing member 103, 203 includes a plurality of mounts 108, 207, each of which being adapted to detachably hold a supporting member 109, 208 for supporting of at least one fluid container 102, 202.

In another embodiment, the system 100, 200 further including a first-time opener 139, 216, adapted for initial opening of the fluid containers 102, 202.

In another embodiment, the system 100, 200 further including at least one device selected from the group consisting of: an opener/closer 145, adapted for raising or lowering of a hinged cap 136 of at least one fluid container 102, 202 with respect to compartment body 137, a stirrer 150, adapted for stirring of a fluid contained in at least one fluid container 102, 203, a reader 134, adapted for reading machine-readable information which at least one fluid container 102, 202 is provided with, a shaker, adapted for shaking of fluids such as magnetically attractable particles contained in at least one fluid container 102, 202, and a washing device, adapted for washing the stirrer 150.

In another embodiment, the for storing and handling of fluid containers 102, 202 is a modular device.

In another embodiment, the storing and handling device 101, 201 further including at least one input/output position 133, 213 for loading/unloading of fluid containers 102, 202 to/from the system.

In another embodiment, the storing and handling device 101, 201 includes two storing members 103, 203 in opposite relationship with respect to each other, wherein the handler 117, 209 being arranged in-between the storing members, adapted for automatically transferring the fluid containers at least with respect to the storing positions of both storing members.

In another embodiment, the storing member 103, 203 is provided with at least one storing position, adapted for pipetting of fluids contained in at least one fluid container 102, 202 stored therein.

In another embodiment, the system 100, 200 further including a pipetting device provided with at least one pipette, adapted for pipetting of fluids contained in at least fluid container 102, 202 when stored in the at least one pipetting position.

In another embodiment, the storing member 103, 203 is comprised of a plurality of modular storing sub-members 106-107, 204-206.

In still another preferred embodiment a modular storing and handling device 101, 201 is provided for storing and handling of fluid containers 102, 202 for use in a system 100, 200 for the automated processing of liquid samples involving mixing of the samples with fluids contained in the fluid containers. The storing and handling device 101, 201 comprises at least one storing member 103, 203 provided with a plurality of storing positions 108, 207, adapted for accommodating the fluid containers 102, 202, the storing member 103, 203 having at least two storing levels 106-107, 204-206, each of which extending in a plane X, Y, which are being stacked in a direction Z orthogonally aligned to the plane X, Y, and a handler 117, 209, adapted for automatically transferring the fluid containers 102, 202 at least with respect to the storing positions 108, 207.

In still yet another preferred embodiment, a method is provided for operating a storing and handling device 101, 201 for storing and handling of fluid containers 102, 202 for use in a system 100, 200 for the automated processing of liquid samples involving mixing of the samples with fluids contained in the fluid containers, the storing and handling device 101, 201 comprising at least one storing member 103, 203 provided with a plurality of storing positions 108, 207, adapted for accommodating the fluid containers, the storing member having at least two storing levels 106-107, 204-206, each of which extending in a plane X, Y, which are being stacked in a direction Z orthogonally aligned to the plane X, Y, in which individual fluid containers 102, 202 are transferred between storing positions of a same or different storing levels in accordance with processing of the liquid samples.

In another embodiment, the individual fluid containers 102, 202 are transferred to at least one pipetting position, adapted for pipetting of fluids contained in the fluid containers for processing of the liquid samples.

In another embodiment, at least one step of the method is selected from the group consisting of: initially opening of at least one fluid container 102, 202; raising of at least one hinged cap 136 of at least one fluid container 102, 202; lowering of at least one hinged cap 136 of at least one fluid container 102, 202; stiffing of the fluid contained in at least one fluid container 102, 202; washing of a stirrer 150; shaking of at least one fluid container 102, 202 for mixing of the fluid contained therein; and reading of at least one machine-readable information which at least one fluid container 102, 202 is provided with, is performed.

Obviously many modifications and variations of the present invention are possible in light of the above description. It is therefore to be understood, that within the scope of appended claims, the invention may be practiced otherwise than as specifically devised.

What is claimed is:

1. A system for automatically processing of liquid samples involving mixing of the samples with fluids, comprising at least one storing and handling device for storing and handling of fluid containers, which includes:

at least one storing member provided with a plurality of storing positions to accommodate said fluid containers, wherein each of said plurality of storing positions are defined by a pair of vertical mount plates each extending in a horizontal direction (X), and wherein said storing member having at least two storing levels, each of which extending in a plane (X, Y) and having multiple of said plurality of storing positions, which are being stacked in a direction (Z) orthogonally aligned to said plane (X, Y), a plurality of pallets slidingly engaged with said storing member and supporting said fluid containers, wherein each of said plurality of pallets slidingly engage one of said pair of vertical mount plates of said plurality of storing positions along said horizontal direction (X), and a handler comprising a transfer head that travels along two directions (Y, Z) and fittingly engages a bottom-side of the plurality of pallets to automatically transfer the fluid containers between said storing positions.

2. The system according to claim 1, wherein said storing and handling device is operable to cool the fluid containers.

3. The system according to claim 1, in which said storing member includes a plurality of mounts, each of which detachably holds a supporting member for supporting of at least one fluid container.

4. The system according to claim 1, further including a first-time opener to initially open said fluid containers.

5. The system according to claim 1, further including at least one device selected from the group consisting of: an opener/closer to raise or lower a hinged cap of at least one fluid container with respect to a compartment body; a stirrer to stir a fluid contained in at least one fluid container; a reader to read machine-readable information which at least one fluid container is provided with; a shaker to shake fluids such as magnetically attractable particles contained in at least one fluid container; and a washing device to wash the stirrer.

6. The system according to claim 1, in which said storing and handling device for storing and handling of fluid containers is a modular device.

7. The system according to claim 1, further including at least one input/output position for loading/unloading of fluid containers to/from the system.

8. The system according to claim 1, in which said storing and handling device includes two storing members in opposite relationship with respect to each other, wherein said handler being arranged in-between the storing members, automatically transfers the fluid containers at least with respect to the storing positions of both storing members.

9. The system according to claim 1, wherein said storing member is provided with at least one storing position to pipette fluids contained in at least one fluid container stored therein.

10. The system according to claim 9, further including a pipetting device provided with at least one pipette to pipette fluids contained in at least one fluid container when stored in said at least one pipetting position.

11. The system according to claim 1, wherein said storing member is comprised of a plurality of modular storing sub-members.

12. A modular storing and handling device for storing and handling of fluid containers for use in a system for the automated processing of liquid samples involving mixing of the samples with fluids contained in said fluid containers, said storing and handling device comprising:

at least one storing member provided with a plurality of storing positions to accommodate said fluid containers, wherein each of said plurality of storing positions are defined by a pair of vertical mount plates each extending in a horizontal direction (X), and wherein said storing member having at least two storing levels, each of which extending in a plane (X, Y) and having multiple of said plurality of storing positions, which are being stacked in a direction (Z) orthogonally aligned to said plane (X, Y);

a plurality of pallets slidingly engaged with said storing member and supporting said fluid containers, wherein each of said plurality of pallets slidingly engage one of said pair of vertical mount plates of said plurality of storing positions along said horizontal direction (X); and a handler comprising a transfer head that travels along two directions (Y, Z) and fittingly engages a bottom-side of the plurality of pallets to automatically transfer the fluid containers between said storing positions.

13. A method for operating a storing and handling device for storing and handling of fluid containers for use in a system for the automated processing of liquid samples involving mixing of the samples with fluids contained in said fluid containers, said storing and handling device comprising at least one storing member, a plurality of pallets, and a handler, wherein said storing member is provided with a plurality of storing positions to accommodate said fluid containers that each are defined by a pair of vertical mount plates that extend in a horizontal direction (X), and said storing member has at least two storing levels, each of which extending in a plane (X, Y) and having multiple of said plurality of storing positions, which are stacked in a direction (Z) orthogonally aligned to said plane (X, Y), said plurality of pallets are slidingly engaged with said storing member, wherein each of said plurality of pallets slidingly engage one of said pair of vertical mount plates of said plurality of storing positions, and said handler comprises a transfer head that travels along two directions (Y, Z), in which said method comprises:

sliding one of said plurality of pallets along said horizontal direction (X) with said handler, while said transfer head is fittingly engaged with one of said plurality of pallets, wherein individual fluid containers are disposed within said one of said plurality of pallets;

removing said one of said plurality of pallets from said storing member with said handler; and transferring said individual fluid containers between storing positions of a same or different storing levels with said handler in accordance with processing of the liquid samples.

14. The method according to claim 13, in which individual fluid containers are transferred to at least one pipetting position, and pipetting fluids contained in the fluid containers for processing of the liquid samples.

15. The method according to claim 14, wherein the method further comprises at least one step selected from the group consisting of: initially opening of at least one fluid container; raising of at least one hinged cap of at least one fluid container; lowering of at least one hinged cap of at least one fluid container; stifling of the fluid contained in at least one fluid container; washing of a stirrer; shaking of at least one fluid container for mixing of the fluid contained therein; and reading of at least one machine-readable information which is provided with at least one fluid container.

16. The method according to claim 13, wherein the method further comprises at least one step selected from the group consisting of: initially opening of at least one fluid container; raising of at least one hinged cap of at least one fluid container; lowering of at least one hinged cap of at least one fluid container; stifling of the fluid contained in at least one fluid container;

washing of a stirrer; shaking of at least one fluid container for mixing of the fluid contained therein; and reading of at least one machine-readable information which is provided with at least one fluid container.

17. The method according to claim 13, further comprising cooling the fluid container with said storing and handling device.

18. The method according to claim 13, wherein said pair of vertical mount plates each comprises a rib for slideable engagement.

19. The method according to claim 13, further comprising providing at least one input/output position for loading/unloading of fluid containers to/from the system.

20. The method according to claim 13, further comprising providing two storing members of said storing and handling device in an opposite relationship with respect to each other, wherein said handler is arranged in-between the storing members; and automatically transferring the fluid containers at least with respect to the storing positions of both storing members.

21. A system for automatically processing of liquid samples involving mixing of the samples with fluids, comprising at least one storing and handling device for storing and handling of fluid containers, which includes:
- at least one storing member provided with a plurality of storing positions to accommodate said fluid containers, said storing member having at least two storing levels, each of which extending in a plane (X, Y), which are stacked in a direction (Z) orthogonally aligned to said plane (X, Y), wherein said storing positions comprise a pipetting position such that, when one of said fluid containers is in the pipetting position, fluid contained within said one of said fluid containers is pippeted, and
- a handler to automatically transfer the fluid containers between said storing positions.

22. A modular storing and handling device for storing and handling of fluid containers for use in a system for the automated processing of liquid samples involving mixing of the samples with fluids contained in said fluid containers, said storing and handling device comprising:
- at least one storing member provided with a plurality of storing positions to accommodate said fluid containers, said storing member having at least two storing levels, each of which extending in a plane (X, Y), which are stacked in a direction (Z) orthogonally aligned to said plane (X, Y), wherein said storing positions comprise a pipetting position such that, when one of said fluid containers is in said pipetting position, fluid contained within said one of said fluid containers is pippeted; and
- a handler to automatically transfer the fluid containers between said storing positions.

23. A method for operating a storing and handling device for storing and handling of fluid containers for use in a system for the automated processing of liquid samples involving mixing of the samples with fluids contained in said fluid containers, said storing and handling device comprising at least one storing member provided with a plurality of storing positions to accommodate said fluid containers, said storing member having at least two storing levels, each of which extending in a plane (X, Y), which are stacked in a direction (Z) orthogonally aligned to said plane (X, Y), wherein said storing positions comprise a pipetting position for pipetting fluid contained within said fluid containers, in which said method comprises:
- transferring said fluid containers from one of said storing positions to said pipetting position of a same or different storing levels with said handler in accordance with processing of the liquid samples; and
- pipetting fluid contained within one of said fluid containers when said one of said fluid containers is in said pipetting position.

* * * * *

UNITED STATES PATENT AND TRADEMARK OFFICE
CERTIFICATE OF CORRECTION

| | | |
|---|---|---|
| PATENT NO. | : 8,361,387 B2 | Page 1 of 1 |
| APPLICATION NO. | : 12/623748 | |
| DATED | : January 29, 2013 | |
| INVENTOR(S) | : Gottlieb Schacher et al. | |

It is certified that error appears in the above-identified patent and that said Letters Patent is hereby corrected as shown below:

Title page, item [30] Foreign Application Priority Data: "EP 08170322" should read
--EP 08170322.5--;

In the Specifications:

Col. 6, Line 6, "stiffing" should read --stirring--;

Col. 7, Line 48, "in at least fluid container" should read --in at least one fluid container--;

Col. 7, Line 53, "information which at least one fluid container is labelled with" should read --information on which at least one fluid container is labelled.--;

Col. 10, Line 67, "must be brake open" should read --must be broken open--;

Col. 16, Line 46, "stiffing" should read --stirring--;

In the Claims:

Col. 18, Line 44, Claim 15, "claim 14" should read --claim 13--;

Col. 18, Line 49, Claim 15, "stifling" should read --stirring--;

Col. 18, Line 54, Claim 16, "claim 13" should read --claim 14--; and

Col. 18, Line 59, Claim 16, "stifling" should read --stirring--.

Signed and Sealed this
Third Day of September, 2013

Teresa Stanek Rea
*Acting Director of the United States Patent and Trademark Office*